United States Patent [19]

Müller

[11] 4,255,571

[45] Mar. 10, 1981

[54] CATALYTIC DEHYDROGENATION PREPARATION OF 3-PYRIDAZONES

[75] Inventor: Werner H. Müller, Eppstein/Taunus, Fed. Rep. of Germany

[73] Assignee: Hoechst Aktiengesellschaft, Frankfurt am Main, Fed. Rep. of Germany

[21] Appl. No.: 971,431

[22] Filed: Dec. 20, 1978

[30] Foreign Application Priority Data

Dec. 24, 1977 [DE] Fed. Rep. of Germany ....... 2757923

[51] Int. Cl.$^3$ .............................................. C07D 237/14
[52] U.S. Cl. .................... 544/239; 544/240; 544/241
[58] Field of Search ................................ 544/239, 240

[56] References Cited

U.S. PATENT DOCUMENTS 3,481,987   12/1969   Ennis et al. .................. 260/306.7 R

OTHER PUBLICATIONS

Tisler et al., Adv. Het. Chem. 9, p. 221 (1960).
Chattergee et al., Tet. Letters 1969, 5223–5224.
Shamma et al., J. Organic Chem. 26, 2586–2587 (1961).

*Primary Examiner*—Mark L. Berch
*Attorney, Agent, or Firm*—Curtis, Morris & Safford

[57] ABSTRACT

Pyridazones are prepared by heating 4,5-dihydro-3-pyridazones in the liquid phase in the presence of a dehydrogenation catalyst. The reaction temperature is in the range of from 150° to 350° C. The dehydrogenation catalyst contains a noble metal of subgroup 8 of the periodic table, which is generally supported on a carrier. The reaction is preferably carried out in the presence of a solvent.

15 Claims, No Drawings

CATALYTIC DEHYDROGENATION PREPARATION OF 3-PYRIDAZONES

The present invention relates to a process for the preparation of 3-pyridazones.

3-Pyridazones are used as intermediates for the synthesis of pharmaceuticals and plant protective agents (cf. British Pat. No. 1,157,045 and German Offenlegungsschrift No. 2,331,398).

It is known to prepare substituted 6-phenyl-3-pyridazones by reacting benzoylacrylic acids with hydrazine (J.Chem.Soc., 1965, 3347). This process, however, gives low yields, since mainly trans-isomers are formed in the usual synthesis of benzoylacrylic acids, which, in contradistinction to the cis-isomers, do not react in the desired manner. In the reaction of the unsubstituted benzoylacrylic acid with hydrazine only the hydrazone of the benzoylacrylic acid according to Grabiel et al., Ber. 32, 396, is formed, not 6-phenyl-3-pyridazone.

It is further known to prepare 6-phenyl-3-pyridazones from 4,5-dihydroderivatives thereof by oxidation with elementary bromine (J.Am.Chem.Soc., 75, 1117 (1953), Ber. 32, 399). The process has the disadvantage that the pyridazones are obtained as hydrobromides they must be liberated by a treatment with bases. The salts formed in this process must be recovered from the waste water by an expensive treatment for cost and environmental protection related reasons.

6-Methyl-3-pyridazone has further been prepared by dehydrogenation of 6-methyl-4,5-dihydro-3-pyridazone in a 10 or 20% yield using nitrous acid or chromium trioxide (W. G. Overend and L. F. Wiggins, J.Chem.Soc. 1947, 239).

Finally it is known to obtain aminophenylpyridazones by oxidation of 4,5-dihydroderivatives thereof with nitrobenzenesulfonic acid (German Offenlegunsschrift No. 1,670,043).

All of the mentioned oxidants are expensive and difficult to handle and cause considerable pollution, when present in the waste water.

A process has now been found for the preparation of 3-pyridazones of the formula

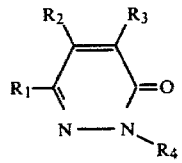

wherein the radicals $R_1$ to $R_4$, which are the same or not all the same, each is hydrogen, straight chain, branched or cyclic alkyl or aryl, which comprises heating 4,5-dihydro-3-pyridazone of the formula

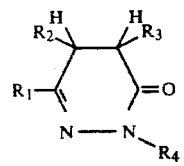

wherein $R_1$ to $R_4$ are as defined above, in the liquid phase and in the presence of a dehydrogenation catalyst containing a noble metal of subgroup 8 of the periodic table, to a temperature of from 150° to 350° C.

Suitable straight chain, branched or cyclic alkyl groups are generally those having up to 12, in particular up to 6, carbon atoms.

The alkyl radicals may be substituted, for example by halogens, in particular fluorine, chlorine or bromine, or by phenyl, naphthyl, hydroxy, alkoxy (preferably having up to 6 carbon atoms) or trifluoromethyl.

Suitable aryl radicals are, for example unsubstituted phenyl or phenyl substituted by halogen or hydroxy, alkoxy or alkyl of up to 6 carbon atoms, or trifluoromethyl or pentafluoroethyl.

Suitable noble metals of subgroup 8 are in particular palladium, platinum, ruthenium, rhodium and iridium. These catalysts are generally used on carriers such as carbon, aluminum oxide, silicic acid, aluminosilicate, magnesium silicate, chromium oxide, chromia-alumina, spinels, zeolites, magnesium oxide, calcium oxide, titanium dioxide and asbestos. Palladium and/or platinum on carbon, $SiO_2$, $Al_2O_3$, chromia-alumina, aluminosilicates, spinels or zeolites are used preferably. The concentration of the noble metal in this case is advantageously in the range of from 0.2 to 20 weight %, calculated on the weight of the carrier, preferably of from 0.1 to 10 weight %. The catalyst contains preferably, in addition to the noble metal chromium as cocatalyst, in particular in an amount of from 0.1 to 20 weight %, calculated on the weight of the carrier.

It was not to be expected that pyridazones could be obtained according to the process of the invention in yields that are extremely high for a dehydrogenation process, even when employing catalysts that have been reused very often, since it is known that nitrogen compounds frequently act as poisons for noble metal catalysts.

The starting materials of the process of the invention are obtained in excellent yield by reacting the corresponding keto acids, esters or nitrils with a hydrazine hydrate according to the following scheme:

(R = H or alkyl)

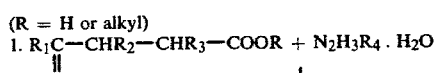

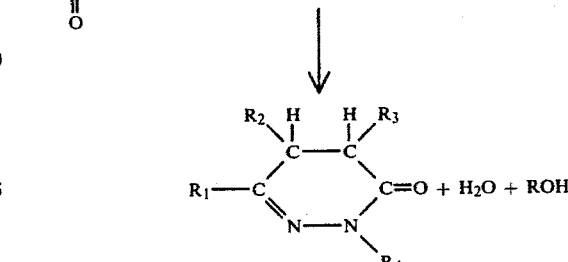

-continued

2. $R_1\overset{O}{\overset{\|}{C}}-CHR_2-CHR_3-CN \;+\; N_2H_3R_4 \cdot H_2O$

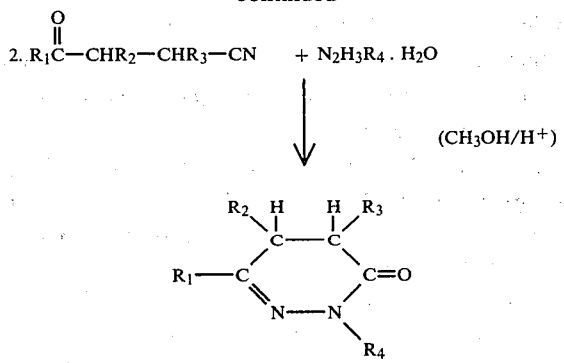

(CH$_3$OH/H$^+$)

The keto acids, esters or nitriles used for this purpose may be prepared according to the Friedel-Crafts acylation of aromatic compounds with succinic acid anhydride or by adding acrylonitriles or acrylic esters to aldehydes in the presence of cyanide or thiazolium salt catalysts:

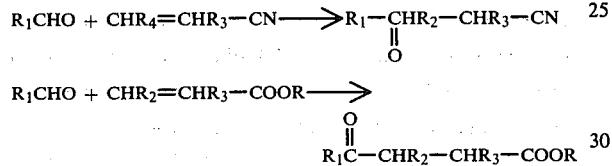

The process of the invention may be carried out discontinuously or continuously, at a temperature of from 150° to 350° C. Temperatures of from 180° to 270° C. are employed preferably, since they allow the obtaining of a particularly high selectivity, while the dehydrogenation proceeds very quickly.

The reaction pressure is generally in the range of from 0.01 to 20 bars.

The partial pressure of the hydrogen formed during the dehydrogenation is preferably kept low in order that the equilibrium may shift in favor of the dehydrogenation and that a hydrogenation of the starting compounds and of the final products may be avoided. This low hydrogen partial pressure can be achieved by flushing the reaction system with an inert gas such as nitrogen, argon or carbon dioxide. The process is preferably carried out in the presence of a solvent. Suitable solvents are, by way of example, hydrocarbons, aliphatic and aromatic ethers, esters and amides. Preferred solvents are aliphatic and aromatic ethers, esters and amides such as ethylene glycol dialkyl ethers, diethylene glycol dialkyl ethers, triethylene glycol dialkyl ethers, diphenyl ether, ethylene glycol diacetate, propanediol diacetate, butanediol diacetate, diethylene glycol diacetate, cyclohexylpropionate, succinic acid dialkyl-(C$_1$–C$_6$) esters, glutaric acid-(C$_1$–C$_6$)-dialkyl esters, dimethylformamide, dimethylacetamide, N-methylpyrrolidone, N-methyl-formanilide, adipic acid-(C$_1$–C$_6$)-dialkyl esters.

Especially preferred are diethylene glycol dialkyl ethers and triethylene glycol dialkyl ethers, having alkyl groups with up to 6 carbon atoms, for example diethylene glycol dimethyl ether (diglyme), triethylene glycol dimethyl ether (triglyme), diethylene glycol diethyl ether, triethylene glycol diethyl ether, diethylene glycol dibutyl ether, diethylene glycol methylbutyl ether (=methylbutyldiglycol), triethylene glycol methylbutyl ether and diphenyl ether.

The process of the invention may be carried out for example with the use of a fixed bed supported catalyst or with the use of a supported catalyst which is kept in suspension in the reaction solution by stirring.

In the case of a discontinuous reaction course, the reaction mixture comprising the solvent, the catalyst and dihydropyridazone is heated, with stirring, preferably under reflux, until off-gas is formed no longer. The stirrer is then stopped, the hydrogen atmosphere is displaced by nitrogen and the solution, still hot, is separated from the deposited catalyst. During cooling the pure pyridazone is obtained as crystals which are then filtered. To the mother liquor is added fresh dihydropyridazone and the solution is then recycled to the reactor. After 10 to 15 tests fresh solvent obtained by distillation of the mother liquor is used. The by-products can be found in the distillation residue.

In the case of a continuous reaction course, a solution of a dihydropyridazone is generally fed continuously to the dehydrogenation reactor containing a fixed catalyst or a catalyst kept in suspension by stirring, while a corresponding quantity of the reaction mixture which substantially contains the formed pyridazone, is discharged. In this process the catalyst is either retained in the reactor by a separator or it is recycled to the reactor after having been separated from the reaction mixture, for example by means of a centrifuge or a decanter. The pyridazone obtained forms crystals during cooling of the discharged reaction mixture and may then be obtained in pure form by filtration. When using those solvents that are indicated above as being particularly preferred, namely di- or triethylene glycol dialkyl ethers, it turns out surprisingly that the dihydropyridazones are more soluble than the pyridazones to be prepared. Hence, the pyridazones precipitate from the reaction solution in pure form, even when the conversion is not complete. Since the main portion of the mother liquor is recycled to the reactor after addition of fresh dihydropyridazone, the reaction need not be continued until such time as the conversion is complete, thereby affording a considerable time-economy. The fact that the pyridazone crystallizes particularly easily out of the preferred solvents has proved especially advantageous since this makes it possible to avoid the energy-intensive distillation to remove the solvent. In the case of a continuous reaction only a relatively low portion of the mother liquor is discharged and worked up by distillation after crystallization of the pyridazone. The solvent recovered thereby in its pure state is recycled.

The present process makes it possible to convert the readily accessible dihydropyridazones into pyridazones by a catalytical reaction that can be carried out in simple manner technically. The pyridazones are obtained in a good yield and can be isolated from the reaction solution in simple manner. The catalysts used for the reaction are distinguished by a high activity, a high stability and a long service life.

The following Examples illustrate the invention.

EXAMPLES

Preparation of the dihydropyridazones (a) 6-Phenyl-4,5-dihydro-3-pyridazone (prepared according to Ingolf Crossland et al., Acta Chemica Scandinavia 19, 1652 to 1660) (1965) and 178 g (1 mol) of β-benzoylpropionic acid (prepared according to Org-.Syn.Coll., Vol. II, 81 (1943), in a 90% yield) were dissolved in a solution of 62.5 g of 80% hydrazine hydrate (1 mol) in 500 ml water and heated for 2 hours to 100° C. After cooling, the white crystals formed were suction-filtered and washed with cold water. The yield was 170 g which corresponds to 97.2% of the theory. Melting point 151° C.

(b) 6-Methyl-4,5-dihydropyridazone was prepared analogously from levulinic acid and hydrazine hydrate. In this process the product precipitated as a hydrate (melting point 80° C.) that was dehydrated in a vacuum drying cabinet at 80° to 100° C. The melting point was 103° C.

Preparation of the pyridazones

Example 1

100 ml of methyl butyl diglycol, 10 g of 6-phenyl-4,5-dihydro-3-pyridazone and 10 g of a catalyst containing 1.3 weight % of palladium on chromia-alumina (19 weight % $Cr_2O_3$ on highly active alumina $Al_2O_3$) were placed in a 250 ml three-necked flask equipped with a stirrer, a thermometer, a reflux condenser and a gas collecting vessel and were then refluxed for 5 hours at 215° to 220° C. whereupon 1.5 liter of gas evolved. After stopping the stirrer, the reaction mixture was allowed to cool to 150° to 160° C., whereby the catalyst precipitated. The supernatant solution over the catalyst was separated and cooled to 50° C., whereupon 3.8 g of 6-pyridazone precipitated. The melting point was 190° C.

The mother liquor was fortified with a further 10 g of starting substance and fed again to the three-necked flask containing the catalyst. After repetition of the test, 8.3 g 6-phenylpyridazone having a melting point of 198° C. precipitated. After the second repetition the yield was 94% and the melting point 200° C.

After the 20th repetition the yield was 90% and the melting point 195° C. For the 21st repetition fresh methylbutyldiglycol was used and the mother liquor was discharged. In this case the yield was only 62% and the melting point had risen to 198° C. Between the 22nd and the 30th repetition the yield was 95% and the melting point had dropped to 190° C. with the 30th repetition. After exchange of the mother liquor for fresh solvent the melting point rose again to 198° C. After the 40th repetition the yield was 93% and the melting point was 194° C. Up to this time a decrease of the activity or of the selectivity of the catalyst could not be observed; on the contrary, the activity had increased in the course of the tests so that the time required for dehydrogenating had dropped from initially 5 hours to 2 hours. It was especially surprising that the catalyst was not poisoned, although the portion of by-products in the mother-liquor was allowed to increase considerably, since new solvent was added only after every 10th test, approximately, to replace the mother liquor.

Example 2

The test was performed as in Example 1, using, however, 2.6 g of catalyst which contained 5 weight % of Pd on $Al_2O_3$.

The mother liquor was replaced by fresh methylbutyldiglycol after every 10th test.

The mean yields until the 25th test were 92%. The melting points dropped from 200° C. (fresh methylbutyldiglycol) to 195° C. (shortly before discharging the mother liquor). The reaction time decreased from 4 hours initially to 3 hours.

Example 3

The test procedure was as in Example 1, using, however, 13 g of catalyst which contained 1 weight % Pd on $SiO_2$ (120 $m^2$ BET surface).

The main yield determined for 20 tests, was 96.2%. The melting point had dropping from 198° C. to 190° C. in the 13th test and rose again to 198° C. in test 14 after renewal of the solvent. The reaction time was 3 to 4 hours. The waste gas consisted of 99% hydrogen.

Example 4

The procedure was as in Example 1, using, however, 26 g, catalyst which contained 0.5 weight % Pd and 1.0 weight % Cr on lithium-aluminum spinel. The mean yield from test 3 to test 8 was 97.8% 6-phenylpyridazone and the melting point was 198° C.

Example 5

The procedure was as in Example 1, using, however, 100 ml of diethylene glycol diethyl ether (boiling point 192° C.) as solvent. The yield rose from 42% in test 1 to 92% in test 3. The melting point was 198° C.

Example 6

The procedure was as in Example 1, using, however, 100 ml of diphenyl ether as solvent. It involved refluxing the reaction mixture for 2.5 hours at 225° C.

The yield rose from 68% in test 1 to 98% in test 3. The melting point was 197° C.

Example 7

The procedure was as in Example 1, using, however, 10 g of 6-methyl-4,5-dihydro-3-pyridazone (melting point 103° C.).

The reaction mixture was heated for 5 hours to the reflux (215° to 218° C.) whereby about 2.5 liter of gas evolved.

The reaction solution was then separated from the catalyst at 130° C., cooled to 150° C. and separated from the crystallized 6-methyl-3-pyridazone by filtration. The filtrate was recycled to the reaction flask after the addition of 10 g 6-methyl-4,5-dihydro-3-pyridazone. The yield of 6-methyl-3-pyridazone after the first test was 66%, after the second 68% and after the third 92%, of the theory. The melting point was 136°–139° C.

What is claimed is:

1. A process for the preparation of a 3-pyridazone of the formula

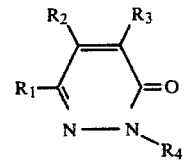

wherein $R_1$ to $R_4$, which are the same or not all the same, each is hydrogen, unsubstituted alkyl, alkyl mono-substituted by halogen, alkyl mono-substituted by phenyl, alkyl mono-substituted by naphthyl, alkyl mono-substituted by hydroxy, alkyl mono-substituted by alkoxy or alkyl mono-substituted by trifluoromethyl, said alkyl being straight chain, branched or cyclic, aryl, aryl mono-substituted by halogen, aryl mono-substituted by hydroxy, aryl mono-substituted by alkoxy of up to 6 carbon atoms, aryl mono-substituted by alkyl of up to 6 carbon atoms, aryl mono-substituted by trifluoromethyl or aryl mono-substituted by pentafluoroethyl, which comprises heating a 4,5-dihydro-3-pyridazone of the formula

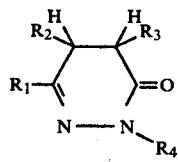

in the liquid phase and in the presence of a dehydrogenation catalyst containing a noble metal of sub-group 8 of the Periodic Table, to a temperature of from 150° to 350° C.

2. A process as claimed in claim 1, wherein said dihydro-3-pyridazone is 6-phenyl-4,5-dihydro-3-pyridazone.

3. A process as claimed in claim 1, wherein the noble metal is on a carrier.

4. A process as claimed in claim 3, wherein the concentration of the noble metal is in the range of from 0.02 to 20 weight %, calculated on the weight of the carrier.

5. A process as claimed in claim 3, wherein the dehydrogenation catalyst contains additionally from 0.1 to 20 weight % of chromium, calculated on the weight of the carrier.

6. A process as claimed in claim 1, wherein said dihydro-3-pyridazone is 6-methyl-4,5-dihydro-3-pyridazone.

7. A process as claimed in claim 1, which further comprises heating at a pressure of from 0.01 to 20 bars.

8. A process as claimed in claim 1, which further comprises heating the 4,5-dihydro-3-pyridazone in a solvent selected from the group consisting of hydrocarbons, aliphatic ethers, aliphatic esters, aliphatic amides, aromatic ethers, aromatic esters and aromatic amides.

9. A process as claimed in claim 1, wherein said unsubstituted alkyl and mono-substituted alkyl are of up to 12 carbon atoms.

10. A process as claimed in claim 1, wherein said unsubstituted alkyl and mono-substituted alkyl are of up to 6 carbon atoms.

11. A process as claimed in claim 1, wherein said metal is selected from the group consisting of palladium, platinum, ruthenium, rhodium and iridium.

12. A process as claimed in claim 3, wherein said carrier is selected from the group consisting of carbon, aluminum oxide, silicic acid, aluminosilicate, magnesium silicate, chromium oxide, chromia-alumina, spinels, zeolites, magnesium oxide, calcium oxide, titanium oxide and asbestos.

13. A process as claimed in claim 18, wherein said temperature is of from 180° to 270° C.

14. A process as claimed in claim 8, which comprises heating the 4,5-dihydro-3-pyridazone in a solvent selected from the group consisting of diethylene glycol dialkyl ethers and triethylene glycol dialkyl ethers, the alkyl moieties of which are up to 6 carbon atoms, and diphenyl ether.

15. A process as claimed in claim 11, wherein the catalyst is palladium.

* * * * *